US 6,558,521 B1

(12) United States Patent
Riley et al.

(10) Patent No.: US 6,558,521 B1
(45) Date of Patent: May 6, 2003

(54) PACKAGE FOR ELECTROPHORESIS GELS

(75) Inventors: Mary S. Riley, Rockland, ME (US); Richard Provonchee, Cushing, ME (US)

(73) Assignee: CBM Intellectual Properties, Inc., Reno, NV (US)

( * ) Notice: Subject to any disclaimer, the term of this patent is extended or adjusted under 35 U.S.C. 154(b) by 0 days.

(21) Appl. No.: 09/577,929

(22) Filed: May 24, 2000

Related U.S. Application Data

(63) Continuation-in-part of application No. 09/177,469, filed on Oct. 23, 1998, now Pat. No. 6,090,255.

(51) Int. Cl.$^7$ .................. G01N 27/26; G01N 27/447
(52) U.S. Cl. ................. 204/456; 204/466; 204/467; 204/606; 204/616; 204/618
(58) Field of Search .................. 204/456, 466, 204/467, 470, 606, 616, 618

(56) References Cited

U.S. PATENT DOCUMENTS

| | | | |
|---|---|---|---|
| 4,314,897 A | 2/1982 | Monte et al. | 206/449 |
| 4,762,743 A | 8/1988 | von Alven et al. | 428/156 |
| 5,085,758 A | 2/1992 | Guadagno et al. | 206/449 |
| 5,217,593 A | 6/1993 | MacConnell | 204/457 |
| 5,384,025 A | 1/1995 | Blasband | 204/619 |
| 5,443,704 A | 8/1995 | Kirkpatrick et al. | 204/620 |
| 5,837,288 A | * 11/1998 | Sylvester et al. | 424/484 |
| 6,036,021 A | * 3/2000 | Moi | 206/570 |
| 6,090,255 A | * 7/2000 | Riley et al. | 204/467 |

\* cited by examiner

*Primary Examiner*—Jill Warden
*Assistant Examiner*—John S. Starsiak, Jr.
(74) *Attorney, Agent, or Firm*—Drinker Biddle & Reath LLP

(57) ABSTRACT

A packaging arrangement is disclosed for protecting an electrophoresis gel from damage during shipment and storage. The package arrangement includes first and second sheets that are sealed about their respective edges to form an enclosed cavity. The cavity is at least partially evacuated of air. An electrophoresis gel is located within the cavity. A support sheet may be disposed between the electrophoresis gel and the package to facilitate removal of the gel and to further stiffen the package. In one embodiment of the invention, a plurality of electrophoresis gels are disposed within the cavity. Each gel is preferably separated from adjacent gels by a spacer. In another embodiment of the invention, the gel is disposed within a tray which, in turn, is located within the cavity.

33 Claims, 4 Drawing Sheets

PACKAGE FOR ELECTROPHORESIS GELS

RELATED APPLICATIONS

This application is a continuation-in-part of patent application Ser. No. 09/177,469, entitled "Vacuum Package for Electrophoresis Gel", filed Oct. 23, 1998, now U.S. Pat. No. 6,090,255 which is incorporated herein by reference in its entirety.

FIELD OF THE INVENTION

The present invention relates to packaging for electrophoresis gels and, more particularly, to an improved vacuum sealed package combination for containing and protecting electrophoresis gels during storage, handling and shipment.

BACKGROUND OF THE INVENTION

Most biological macromolecules are electrically charged such that, when subjected to an electrical field, they begin to move, This phenomenon is the basis behind an electrophoresis process wherein a prescribed electrical current is generated adjacent to a collection of macromolecules to produce movement of the macromolecules through a solvent in a particular direction. Since different macromolecules vary in molecular size, weight and charge, it is possible to use an electrophoresis process to distinguish between different macromolecules based on their respective rates of movement through the solvent. Electrophoresis can also be used for other types of macromolecule analysis, such as detecting amino acid changes, nucleic acid sequencing and protein analysis.

One medium that has been used for over thirty years as the carrier for the macromolecules in an electrophoresis process is a gel. Two of the most popular types of gels are agarose and polyacrylamide gels. An electrophoresis gel is typically planar in shape and includes a series of spaced apart wells. The wells are designed to receive the biological sample being tested. In the past, it was customary for the laboratory that was conducting the testing to cast their own gels by hand. It soon became apparent, however, particularly as electrophoresis testing of DNA increased, that it is more convenient and more precise to use precast gel slabs made to uniform composition, size and well configuration standards.

Conventional gels are made from various materials depending on their intended use. One widely used gel material for DNA electrophoresis is agarose. This gel is a sugar based gel that is highly flimsy and subject to tearing and deformation if not handled carefully. Tearing or cracking is especially prone between the wells where the least amount of material is present. Deformation or tearing of the gel can potentially produce inaccuracies during testing. To complicate matters further, the material properties of the gel make detecting hairline cracks very difficult. Hence, proper packaging of the gels is extremely important when shipping or storing the gels.

Several packaging arrangements have been developed in recent years to protect electrophoresis gels during shipment. U.S. Pat. No. 5,443,704 discloses one packaging arrangement for protecting the gels. This packaging arrangement includes a plastic tub within which the gel is placed. A foil-lined cover is adhered to the top of the tub to retain moisture inside the package. It was subsequently determined that the tub alone did not provide sufficient protection for the gel. Filler materials had to be added to the box to provide adequate protection from damage. As a result, this type of packaging arrangement is generally very expensive to produce.

Another prior packaging arrangement for shipping gels includes a pouch formed from foil material that is sealed along each edge. In order to protect the gel, a separate sheet of material is folded over the gel to separate it from the foil. A deficiency with this packaging arrangement is that the package does not adequately protect the gel from damage such as edge deformation and well breakage.

U.S. Pat. No. 5,837,288 discloses one particular type of pouch wherein the pouch is almost completely evacuated of air prior to sealing, resulting in a reduced atmospheric environment (i.e., less than 10% of atmospheric air pressure). Spacers are used on the sides of the gel to prevent the package walls from crushing the sides of the gels.

Co-pending patent application Ser. No. 09/177,469, entitled "Vacuum Package for Electrophoresis Gel", filed Oct. 23, 1998, discloses an alternate package configuration which, in one embodiment, uses a support sheet in combination with a sealed, at least partially evacuated interior to restrain the gel within the package for preventing gel damage during storage and shipping.

A need exists for an improved packaging arrangement which is inexpensive to manufacture and which adequately protects a gel or series of gels from damage during shipment, handling or while stored.

SUMMARY OF THE INVENTION

An object of the invention is to provide a package for an electrophoresis gel which includes sufficient rigidity to prevent damage to the gel and minimize movement of the gel within the package. The wells in the gel make it particularly susceptible to damage and breakage during shipment.

Another object of the invention is to provide a package for an electrophoresis gel which, in one embodiment, includes a support tray that functions as part of the packaging during shipment and can be subsequently used to hold the gel during an electrophoresis process.

These and other objects and advantages of the invention are provided by the packaging arrangement according to the present invention. The packaging arrangement includes first and second sheets that are sealed along their respective edges to form an enclosed cavity. In one embodiment, the cavity is at least partially evacuated of air prior to or after sealing. At least one electrophoresis gel is disposed within the evacuated cavity. The partial evacuation of air from the cavity causes the top and bottom sheets to conform to the gel, thereby restraining it from movement within the package.

In one embodiment of the invention, a tray is incorporated into the package. The gel is located within the tray which, in turn, is located between the top and bottom sheets. The tray includes a base and at least two side walls which extend upward along the longitudinal sides of the gel. The combination of the low pressure environment in the package and the tray produces a rigid packaging configuration that minimizes motion of the electrophoresis gel contained therein.

The foregoing and other features and advantages of the present invention will become more apparent in light of the following detailed description of the preferred embodiments thereof, as illustrated in the accompanying figures.

BRIEF DESCRIPTION OF THE DRAWINGS

For the purpose of illustrating the invention, the drawings show a form of the invention which is presently preferred. However, it should be understood that this invention is not limited to the precise arrangements and instrumentalities shown in the drawings.

DETAILED DESCRIPTION OF THE EMBODIMENTS

While the invention will be described in connection with one or more preferred embodiments, it will be understood that it is not intended to limit the invention to those embodiments. On the contrary, it is intended that the invention cover all alternatives, modifications and equivalents as may be included within its spirit and scope as defined by the appended claims.

Figure 1:
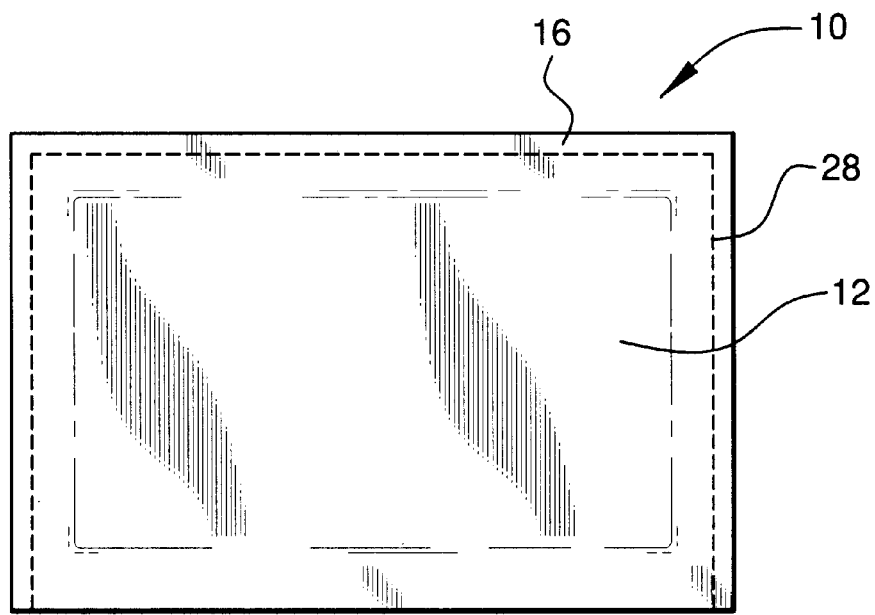
FIG. 1 is a plan view of one embodiment of an electrophoresis gel package according to the present invention.
Figure 2:
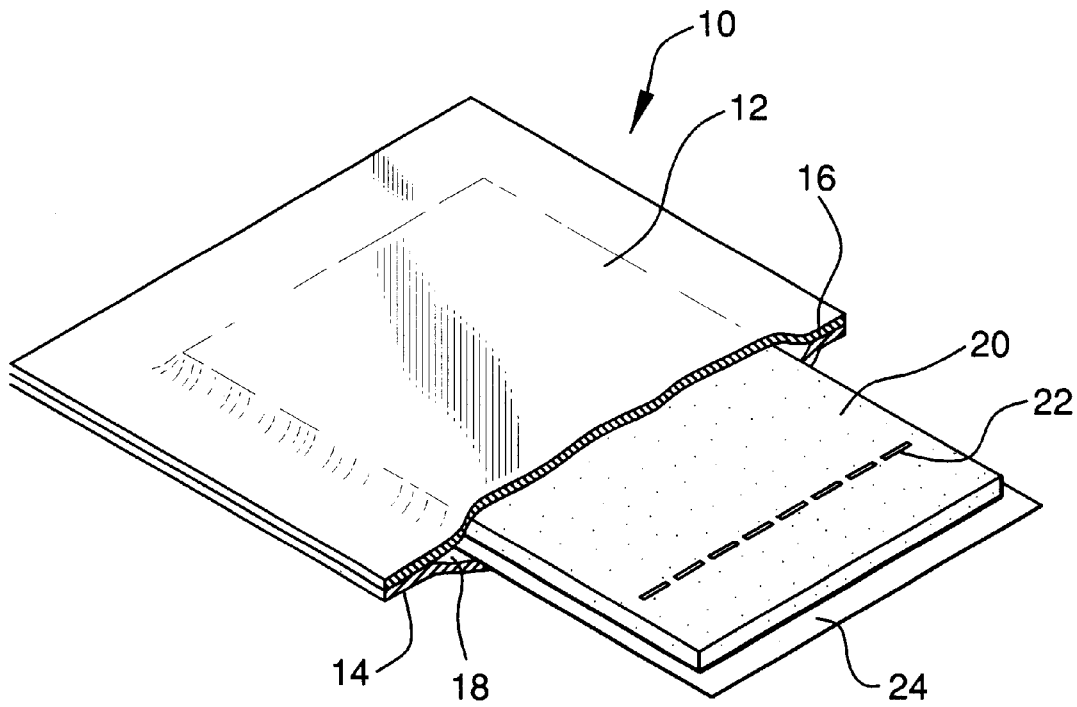
FIG. 2 is a partially broken away isometric view of the electrophoresis gel package, illustrating an electrophoresis gel contained within a partially evacuated cavity.

Referring now to the drawings, wherein like reference numerals illustrate corresponding or similar elements throughout the several views, FIGS. 1 and 2 illustrate one embodiment of an electrophoresis package 10 according to the present invention. The package 10 is formed from two overlapping sheets 12, 14 that are sealed 16 along their edges to form an enclosed cavity 18. The cavity 18 is designed to contain at least one precast electrophoresis gel 20. One preferred gel 20 for use in the present invention is an agarose gel, such as 1% SeaKem® LE, sold by BioWhittaker Corporation, Rockland, Me.

In order to prevent the gel from moving during shipment, the package 10 is vacuum sealed 16 along its edges so that the sheets 12, 14 substantially conform to the shape of the gel 20. That is, the cavity 18 within the package 10 is preferably at least partially evacuated of air. Removal of air from within the package 10 stiffens the sheets 12, 14, thereby increasing the package's strength to better support the gel.

Most conventional sealed packages are not evacuated prior to sealing. As such, the residual air contained within the package results in the upper and lower sheets of the package essentially functioning independent from one another, i.e., they do no support one another. The independent movement of the sheets reduces the package's stiffness and allowing it to be easily flexed. The relative ease with which non-evacuated pouches can be flexed increases the chance that the malleable gel contained within the package will become damaged.

Additionally, the air trapped within a conventional package produces an interior volume which is considerably larger than the gel. Accordingly, the gel is generally free to move within the package. Gels are inherently slippery and some gels actually exude moisture, making them even more prone to sliding within the package. Since the gel is very soft and pliable, movement during shipment or storage increases the likelihood of damage to the gel.

The evacuated package design according to the present invention reduces damage to the gel 20 by stiffening the packaging and reducing the mobility of the gel. The vacuum packing/sealing of the packaging eliminates at least a partial amount of the residual air contained within the cavity 18 of the package 10 after formation. Preferably between about 1% to about 89% of the air within the package 20 is removed prior to sealing which causes the sheets to conform to the shape of the gel without crushing the gel. As a result, the upper and lower sheets 12, 14 overlap one another adjacent to the edges of the gel 20 and, thus, effectively function as a substantially unitary structure.

Furthermore, the drawing of the upper and lower sheets 12, 14 of the package 10 against or in close proximity to the top surface of the gel 20 prevents the gel 20 from moving within the package 10 by reducing the interior volume of the cavity 18 after the gel 20 is inserted into the package 10.

The sheets 12, 14 of the package 10 are each made from at least one and, more preferably, several constituent layers. In one embodiment, the layers form a laminate having a thickness of less than approximately 3.0 mil. More preferably, the thickness is about 2.5 mil. In one exemplary embodiment, each sheet 12, 14 includes a metallized outer layer, an intermediate layer and an inner layer. The layers are preferably adhered to one another with a suitable adhesive. Although the following discussion refers to the upper and lower sheets as being similarly configured, they need not be so. For example, the lower sheet 14 can be selected with a different thickness and/or material than the upper sheet 12. Those skilled in the art would readily be capable of making such modifications in light of the teachings provided herein.

One problem associated with agarose type gels, such as 1% SeaKem LE, is that they can deteriorate from loss of moisture when exposed to certain environmental conditions. Hence, it is desirable to protect the gel 20 from moisture loss by forming the package 10 from material that provides a suitable moisture barrier. In one embodiment of the invention, the package 10 is formed from sheet materials with a moisture vapor transmission rate (MVTR) of less than approximately 0.02 grams in 100 square inches over a 24 hour period. This preferred moisture vapor transmission rate allows the gel to remain viable for a 12 month shelf life. The moisture transmission rate is determined by measuring the amount of vapor loss through a 100 $in^2$ piece of the packaging material over a 24 hour period of time while exposed to a temperature of 100° F. This test for determining moisture vapor transmission rate is disclosed in ASTM Standard F1249. More preferably, the moisture transmission rate is about 0.01.

In one exemplary embodiment of the invention, the outer layer is made from metallized polyester or polypropylene material with a thickness of approximately 0.48 mil. The metallized polyester protects the enclosed gel 20 from environmental factors. The outer layer preferably has a smooth surface appearance that accepts customary printing. Although straight foils can be used as the outer layer in the present invention, they are not preferred due to their typical crinkled and pock marked appearance which leads to poor print quality.

The intermediate layer is preferably made from polyester material with a thickness of approximately 0.48 mil. The inner layer is preferably made from low density polyethylene material with a thickness of approximately 2 mil. It is preferable to use low density polyethylene material since it is chemically compatible with an agarose gel. The film in this exemplary embodiment has a moisture transmission rate of about 0.01 grams at 100° F./100 square inches/24 hours.

The upper and lower sheets 12, 14 are sized to provide a cavity 18 within the package 10 that allows the gel 20. As discussed above, a seal 16 is formed along the edges around the package 10 to prevent air leakage. Of course, if the upper and lower sheets 12, 14 are contiguous along one side, i.e., folded over the gel 20, only three sides need to be sealed since the fourth side is inherently sealed. For a 6×10 cm gel, a single gel package 10 according to the present invention, is formed with upper and lower sheets 12, 14 that have a preferred width of approximately 9.91 cm (3.9 inches) and a preferred length of approximately 13.91 cm (5.48 inches). This permits a seal to be formed around the package having a width of preferably between about 0.635 cm (0.25 inches) and about 0.9525 cm (0.375 inches). This will leave an inside spacing of about 1 cm±2 mm all around the edges of the 6×10 cm gel 20.

To further protect the gel 20 from inadvertent bending, it may be desirable to incorporate of one or more support sheets 24. In one embodiment of the invention, a support sheet 24 is located under the gel 20 and provides a semi-rigid backing for the gel 20. The support sheet 24 preferably has a length and width at least that same as the gel 20. More preferably, the support sheet 24 has a length and width that extends past the ends of the gel 20 as shown in FIG. 2. The added dimensions on the support sheet 24 help to prevent damage to the edges of the gel 20 during sealing and shipment. A sheet smaller than the dimension of the gel is not desirable. The larger the gel (e.g., 20×25 cm), the more preferable it is to incorporate support sheets 24.

For example, testing has shown that for a 6×10 cm gel is best protected when centered on a support sheet 6.2×10.6 cm±1 mm, and a 10×15 cm gel is best protected when centered on a support sheet 10.2×15.6 cm±1 mm. However, it should be recognized that alternate sizes and shapes for the support sheet 24 are contemplated in the present invention depending on the size and shape of the gel and the users needs.

The support sheet 24 is preferably made from high impact polystyrene material or oriented polystyrene material with a thickness of about 10 mil. One or both surfaces of the support sheet 24 can be textured to minimize movement of the support sheet 24 within the package 10. In one preferred embodiment, the support sheet 24 is textured on the side facing the package 10 and smooth on the side adjacent to the gel 20. Testing has shown that the smooth surface adheres evenly to the gel 20 both when first placed onto the support sheet 24 and after over twelve hours of sitting in a sealed package 10. However, texturing of both sides is also contemplated if desired. It should be recognized that if additional stiffness is desired, an additional support sheet 24 can be incorporated on top of the gel 20. Alternatively, a thicker support sheet 24 can be used if desired.

The use of the support sheet 24 also permits the end user to easily remove the gel 20 from the package 10 since it provides a semi-rigid surface to grab or slide a spatula under. This is especially important for larger size gels 20 which would otherwise be very difficult to handle. If desired, the support sheet 24 as described above can be inserted with the gel 20 into a gel holder that is used to conduct the testing (not shown). Preferably the material from which the support sheet 24 is made has a density of greater than 1.0 to prevent the support sheet 24 from floating if used with the gel 20 during testing. Also, depending on the process used to initially insert the gel 20 into the package 10, the support sheet 24 can be used to facilitate such insertion. It is preferable that the support sheet material be ultraviolet light transparent to allow the user to photograph the gel 20 while on the sheet 24.

Figure 5:
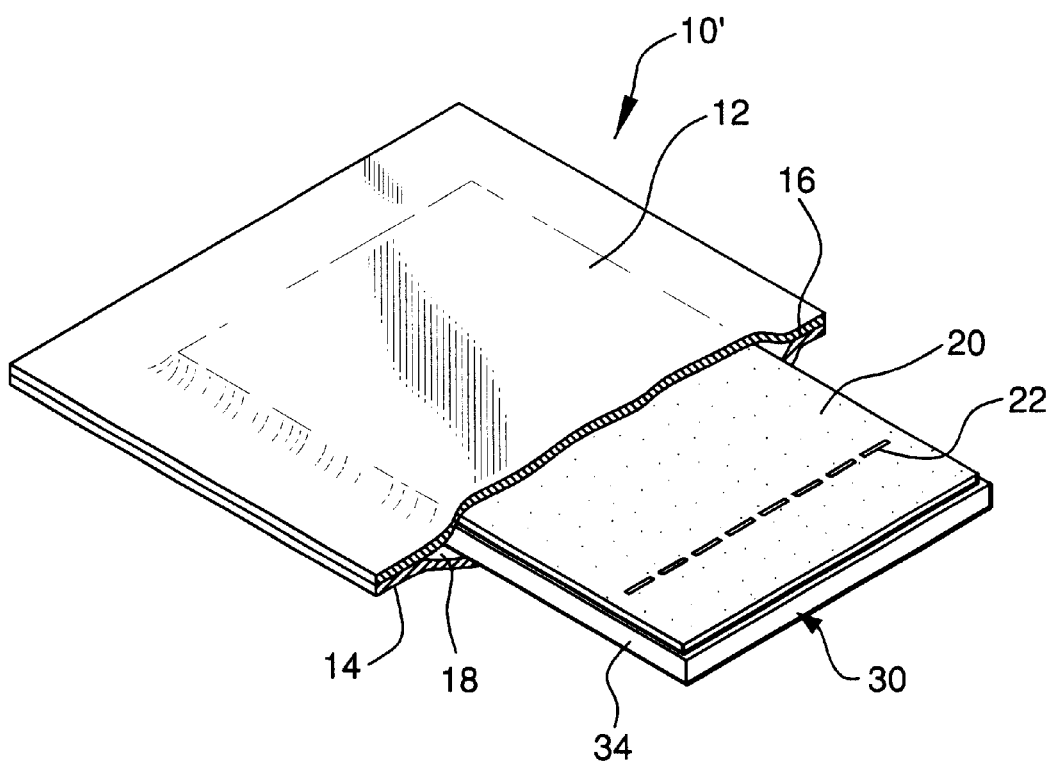
FIG. 5 is a partially broken away isometric view of an alternate embodiment of the electrophoresis gel package, illustrating an electrophoresis gel contained within a tray in a partially evacuated cavity.
Figure 6A:
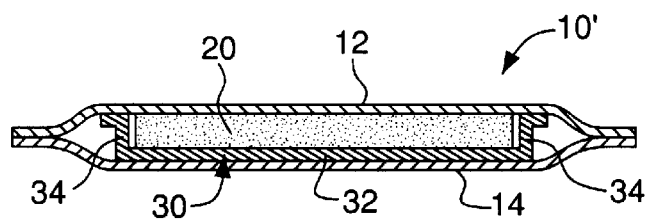
FIG. 6A is a cross-sectional view of the electrophoresis gel package of FIG. 5.
Figure 6B:
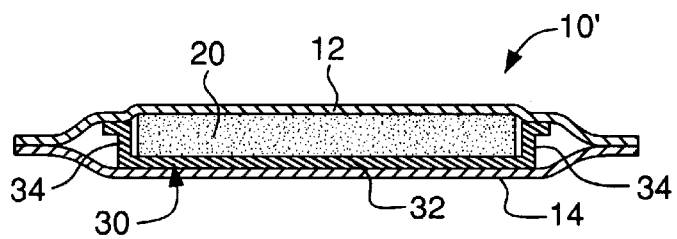
FIG. 6B is a cross-sectional view of the electrophoresis gel package of FIG. 5 that includes a tray with short side walls.

In an alternate embodiment of the invention shown in FIGS. 5 and 6A and 6B, a support tray 30 is incorporated into the package 10' to further stiffen the package 10' and protect the electrophoresis gel 20. In this embodiment, the gel 20 is preferably disposed or cast in the tray 30. The tray 30 includes a base 32 and at least two side walls 34 integrally formed with the base 32 and spaced apart from one another to receive a gel 20 therebetween. More preferably, there are four side walls 34 formed around the base 32. The tray 30 is designed to prevent pinching or crushing of the edges of the gel 20. More specifically, in a sealed package, the edges of the package angle toward one another at the seal. If the gel contained within such a package should migrate toward that sealed edge during shipping, the taper of the edges could cause crushing or pinching of the edge of the gel resulting in de-watering of the gel. Gels with such deformities can produce sample irregularities during use, such as sample migration.

To prevent this occurrence, the present invention incorporates a tray into one embodiment of the package 10' which is designed to maintain the gel 20 at a uniform thickness until it is desired to be used. The tray also provides additional stiffness to the package 10' to minimize bending of the gel 20.

A preferred tray 30 for use in the present invention is slightly larger that the gel 20 so as to provide a snug fit between the gel 20 and tray 30. However, in order to accommodate dimensional variations in the gel, the tray 30 is more preferably between about 1% to 2% longer than the gel 20, between about 1% to 2% wider than the gel 20, and has side walls 34 that have a height equal to (FIG. 6A) or slightly shorter than (between about 1% to about 5%) (FIG. 6B) the height of the gel 20 when the gel is placed within the tray 30. While the side walls 34 can be slightly taller than the height of the gel 20, doing so will reduce the contact between the top sheet 12 of the package and the top surface of the gel 20 when sealed. As such, the resulting constraint that such contact provides is lessened. It is not desirable to make the length or width of the tray shorter than the gel 20 since doing so will result in gel compression and deformation of the wells.

It is also preferable that the tray 30 not include any sharp corners which can damage the gel 20 or puncture the package 10'. Accordingly, in one embodiment of the invention (shown in FIGS. 6A and 6B), the package 10' includes a small flange 36 around the top of the side walls and includes radii on all the corners. It should be recognized that thicker package materials could eliminate the need for radii on the edges and a flange.

The tray 30 can be formed from any suitable material. Preferably, the tray is made from a plastic material that is reasonably rigid. The rigidity of the tray 30 will vary depending on the material, tray size and thickness. Those skilled in the art would readily be capable of selecting a suitable tray material for use in the present invention in light of the teachings provided herein. In one embodiment, the tray thickness (i.e., the thickness of the base and side walls) is between about 0.010 inches to about 0.040 inches.

In the embodiment of the invention utilizing a tray 30, a support sheet 24 is generally not needed since the tray 30, in combination with the top and bottom sheets 12, 14, provides the necessary rigidity to prevent bending of the gel, and permits the gel to be readily extracted from the package.

As discussed above, the tray side walls 34 are preferably designed so that they are the same size as or slightly smaller than the gel 20 (FIGS. 6A and 6B). As such, the vacuum sealing of the package 10' causes the top sheet 12 to apply a slight downward pressure on the top surface of the gel 20. The downward pressure on the gel 20 locks it into place within the tray, thereby inhibiting movement. The height of the side walls 34 prevent the pressure from the top sheet 12 from crushing the gel 20. As a result, movement of the gel 20 within the package 10 is minimized.

During development of the present invention, the inventors at first considered vacuum sealing to be inappropriate since it was believed that it would result in loss of moisture from the gel, and would cause the gel to become damaged from compression caused by the packaging. However, testing proved that the process did not cause any appreciable moisture loss and that the packaging materials conformed to the shape of the gel rather than crushing it. The addition of the tray greatly expands the capabilities and resulting rigidity of the package.

Another benefit provided by the packaging configuration according to the present invention is that the increased stiffness provided by the overlapping sheets 12, 14 allows thinner sheets to be used to form the package 10. This results in a packaging arrangement that is less expensive to manufacture. Furthermore, the thinner sheets prevent the gel 20 from being damaged during vacuum forming. For example, if thick sheets of material are used to form the package, they will resist bending when subjected to a vacuum force, more so than a thinner sheet. (The sheets bend to conform to the shape of the gel 20 when the air is evacuated from within the cavity.) Instead of bending, the thicker sheets tend to compress the gel 20. The use of thinner sheets in the present invention allows the sheets 12, 14 to conform more readily to the shape of the gel 20, thereby evacuating more air without damaging the gel 20. The problems described above with respect to thicker sheets may also occur with materials that have relatively high stiffness characteristics, such as polyethylene terephthalate (PET) material.

The incorporation of the tray into the package, on the other hand, permits thicker or stiffer sheets to be used, if desired, since the tray side walls will prevent the top sheet from compressing the gel. Alternately, since the tray adds considerable rigidity to the package, the bottom sheet may be thinner than the top sheet.

Figure 3:
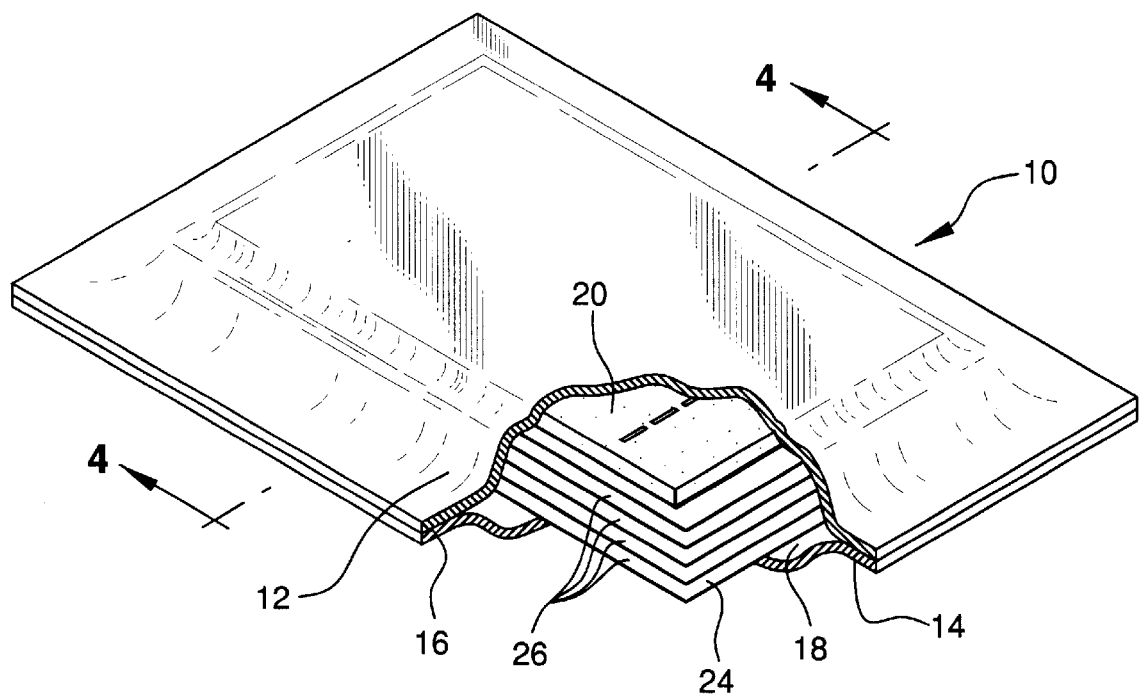
FIG. 3 is a partially broken away isometric view of another embodiment the electrophoresis gel package according to the present invention, illustrating a plurality of electrophoresis gels contained within a cavity.
Figure 4:
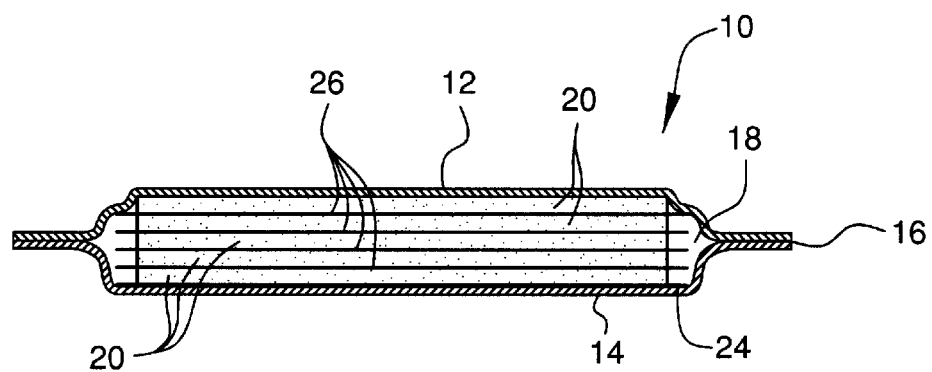
FIG. 4 is a cross-sectional view of the electrophoresis gel package of FIG. 3 illustrating the interleaving of spacer sheets between adjacent gels.
Figure 7A:
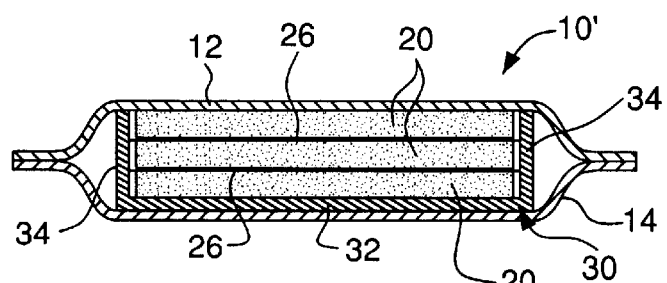
FIG. 7A is a cross-sectional view of one embodiment of the package with multiple gels interleaved by spacers.
Figure 7B:
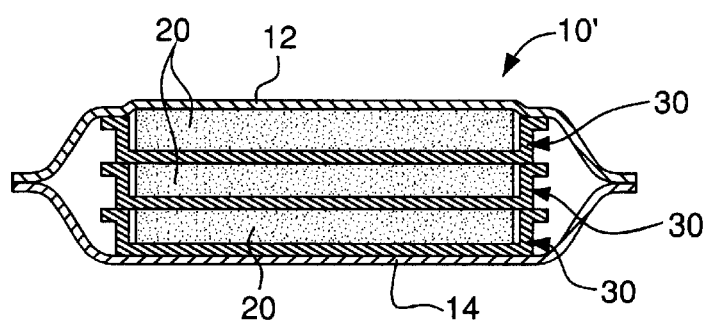
FIG. 7B is a cross-sectional view of another embodiment of the package with multiple gels, each gel contained within an associated tray.

The present invention also contemplates the insertion of multiple gels 20 into the package 10. Referring to FIGS. 3 and 4, an embodiment of the package 10 is shown containing a series of stacked gels 20. FIG. 7A shows an alternate embodiment of the package 10' containing a series of stacked gels 20 within a single tray 30. FIG. 7B illustrates an embodiment of the invention wherein multiple trays, each containing an associated gel, are stacked within the package 10'. In this embodiment, it is contemplated that locking ledges (not shown) may be formed on the bottom of the tray to secure the trays in a stack. The upper and lower sheets 12, 14 and tray of these embodiments are the same as discussed above except that they are larger to accommodate the added number of gels 20.

In order to prevent the gels 20 from adhering to one another, one embodiment of the present invention contemplates the incorporation of spacers 26 interleaved between adjacent gels 20. The spacers 26 are preferably made from high impact polystyrene material or oriented polystyrene material which provides a semi-rigid backing for the gel 20. The spacers 26 are preferably 10 mil thick and are textured on one side to reduce adherence of the spacer 26 to the adjacent gel 20. Although the spacer 26 can be textured on both sides, it is preferable that the spacer is smooth on one side to assist in adhering one gel (i.e., the upper gel) on the spacer 26. Testing has proven that the smooth surface adheres evenly to the gel 20 both when first placed onto the support sheet 24 and after over twelve hours of sitting in a sealed package 10.

The spacers 26 preferably have a length and width at least that same as the gel 20. More preferably, the spacers 26 each have a length and width that extends past the ends of the gel 20, but are less than the inner dimensions of the package (FIG. 3) or tray (FIG. 7A). The added dimensions on the spacers 26 help to prevent damage to the edges of the gel 20 during sealing and shipment. The larger the gel (e.g., 20×25 cm), the more preferable it is to incorporate spacers 26. In addition to separating adjacent gels 20, the spacers 26 permit the gels 20 to be removed one at a time from the package 10 since it provides a semi-rigid surface to grab or slide a spatula under. This is especially important for larger size gels 20 which would otherwise be very difficult to handle. If desired, the spacer 26 can be inserted with the gel 20 into a gel holder that is used to conduct the testing (not shown). Preferably the material from which the spacer 26 is made has a density of greater than 1.0 to prevent the spacer 26 from floating if used with the gel 20 during testing. Also, depending on the process used to initially insert the gel 20 into the package 10, the spacer 26 can be used to facilitate such insertion. It is preferable that the spacer 26 material be ultraviolet light transparent to allow the user to photograph the gel 20 while on the spacer 26.

If further rigidity is needed in the multi-gel embodiment, an end card (not shown) can be used on the top of the stack of gels. The end card is preferably made from plastic material, such as polystyrene or corrugated polyethylene. The end card has a preferred thickness of about 15 mils or more. In one embodiment of the invention, the end card thickness is selected from a range between about 15 mil and about 40 mil. The end card preferably has the same dimensions as described above with respect to the spacer 26. The end card may also be necessary in the single-gel embodiment when the gels are relatively large inasmuch as such gels can be damaged more easily from inadvertent crushing, or from contact with the pouch materials during vacuum sealing or placement and removal of the gel.

In order to form the package 10, the gel 20 is preferably first placed on the bottom sheet 14, and the top sheet 12 is placed on top. For the package configuration 10' that includes a tray 30, the gel is first placed in (or cast in) the tray 30, then the combination is placed between the top and bottom sheets 12, 14. The package 10, 10' is then placed in an evacuation chamber, such as a Ultravac® 2000 chamber, sold by Koch Supplies, Inc., Kansas, Mo. The air is evacuated from the chamber resulting in the air between the first and second sheets 12. 14 also being evacuated. Once a sufficient amount of air is evacuated so as to cause the edges of the sheets to overlie one another, the sides of the package 10, 10' are sealed with a heat seal 16.

In the embodiment of the invention without a tray, a suitable package 10 was produced by operating the Ultravac® 2000 chamber with the following settings: Vac=98; Vacplus=0; Sealing=0.9; Cooling=5/99; and Venting: pulse from 99 to 0. A vacuum of about 27 inches of mercury is used in this embodiment of the invention, which is sufficient to evacuate a package 10 formed from 3 mil upper and lower sheets without damaging the gel 20. During testing it was determined that a vacuum of less than 20 inches of mercury was insufficient to produce a suitable package 10, but that a vacuum of about 23 inches of mercury or more would work well. Of course, a package 10 made from sheets of varying thickness may require more or less or a vacuum to properly evacuate the contained air and conform to the gel without causing damage. It is contemplated that other types of seals and method(s) of evacuating the air from within the package may be substituted for the disclosed method. It is also contemplated that other conventional vacuum sealing technique, such as gas flushing, can be used to form a package according to the present invention provided that the process is tailored to provide sufficient evacuation and sealing without damaging the gel.

It should be readily apparent that the process settings, such as vacuum pressure, length time of vacuum, cooling time, etc., would need to be adjusted depending on the type of vacuum chamber used, the physical characteristics and material properties of the gel, and the packaging material selected. The goal would be to tailor the settings so as to sufficiently evacuate the package 10 while preventing the gel from being crushed. Such modifications and alterations would be readily appreciated by one skilled in the art in light of the instant disclosure.

During testing it was determined that between 1% and about 89% of the air within the package 10 without the tray should be evacuated in order to immobilize the gel within the package 10. More preferably, between about 25% and about 40% of the air within the package should be removed to provide sufficient immobilization of the gel to prevent damage. Those skilled in the art, however, will readily appreciate that the desired amount air to be removed from the package will depend on the size of the gel (larger gels need more air removed because they are heavier and, therefore, are better protected when the package more closely conforms to the gel); the size of the package (a perfectly fitting package does not require the removal of much, if any, air); the stiffness of the package material (which will govern how easily the material drapes over the gel); and whether support sheets are used in the package (support sheets add protection, thus, lessening the amount of evacuation needed).

If the package 10' includes a tray 30, a similar method as described above is carried out to form the package 10'. Between 1% and 99.9% of the air within the package should be evacuated in order to immobilize the gel within the package 10. More preferably, between about 25% and about 50% of the air within the package should be removed to restrain the gel and tray within the package. Once again, those skilled in the art will readily appreciate that the desired amount air to be removed from the package will depend on the various factors described above, as well as the stiffness and shape of the tray being incorporated into the package.

In order to protect the gel 20 from inadvertent damage during opening, the package 10 preferably includes indicia 28 (shown in FIG. 1) formed on the upper and/or lower sheet 12, 14 indicating where the user should cut to avoid contacting the gel. Preferably the indicia 28 instructs the user to open three sides of the package 10. In an alternative embodiment, one or more tear notches (not shown) may be formed in the package 10 providing the user with a easy method for tearing open the package 10.

The present invention provides a novel packaging configuration for protecting an electrophoresis gel from damage during shipment and storage. By vacuum sealing the gel within a durable pouch, the present invention minimizes movement of the gel that would otherwise cause damage. The incorporation of a tray into the package configuration further protects the gel from damage. While the above discussion has described the use of the invention with agarose gels, the present invention is suitable for use with all electrophoresis gels, such as polyacrylamide and similar polymeric materials. Also, while the present invention has applicability to a variety of gel thicknesses, it is particularly useful for gels between 2 mm to 7 mm thick since those gels are especially prone to damage during shipping.

Although the invention has been described and illustrated with respect to the exemplary embodiments thereof, it should be understood by those skilled in the art that the foregoing and various other changes, omissions and additions may be made therein and thereto, without parting from the spirit and scope of the present invention.

What is claimed is:

1. A package comprising
   a first sheet;
   a second sheet sealed to the first sheet along at least three sides so as to form an enclosed cavity, the enclosed cavity being at least partially evacuated of air; and
   at least one electrophoresis gel disposed within the cavity;
   wherein the partially evacuated cavity contains gas having a pressure between about 11% and about 99% of atmospheric pressure.

2. A package according to claim 1 wherein the partially evacuated cavity gas pressure is between about 60% and about 75% of atmospheric pressure.

3. A package according to claim 1 further comprising a tray and wherein the electrophoresis gel is located within the tray.

4. A package according to claim 3 wherein the tray has four side walls formed integral with a base, each side wall having a height less than the height of the electrophoresis gel when the electrophoresis gel is located within the tray.

5. A package according to claim 4 wherein the height of the side walls is between about 1% to about 5% shorter than the height of the electrophoresis gel when the electrophoresis gel is located within the tray.

6. A package according to claim 4 wherein the length and width of the tray are each between about 1% to about 2% larger than the length and width of the gel.

7. A package according to claim 4 wherein the tray has a wall thickness between about 0.010 inches and about 0.040 inches.

8. A package according to claim 3 wherein a plurality of electrophoresis gels are disposed within the tray.

9. A package according to claim 3 wherein a plurality of electrophoresis gels and trays disposed between the first and second sheets, each gel being located in an associated tray.

10. A package according to claim 1 wherein the at least one electrophoresis gel is an agarose gel.

11. A package according to claim 1 further comprising a support sheet disposed between at least one electrophoresis gel and the first sheet.

12. A package according to claim 1 wherein a plurality of electrophoresis gels are disposed within the cavity.

13. A package according to claim 12 wherein a spacer is located between adjacent electrophoresis gels.

14. A package according to claim 1 wherein the first sheet includes an outer layer of metallized polyester adhered to an inner layer of polyethylene.

15. A package comprising
a first sheet;
a second sheet sealed to the first sheet along at least three sides so as to form an enclosed cavity, the enclosed cavity being at least partially evacuated of air;
at least one electrophoresis gel disposed within the cavity; and
a tray;
wherein the electrophoresis gel is located within the tray; and
wherein the tray has at least two opposed side walls, the side walls having a height no larger than the height of the electrophoresis gel when the gel is located within the tray.

16. An electrophoresis gel package comprising:
a pouch formed from first and second sheets that are sealed to one another along their edges to form an enclosed cavity, the cavity being at least partially evacuated of air; and
at least one electrophoresis gel disposed within the cavity;
wherein the partially evacuated cavity contains gas having a pressure between about 11% and about 99% of atmospheric pressure.

17. A package according to claim 16 wherein the partially evacuated cavity gas pressure is between about 60% and about 75% of atmospheric pressure.

18. A package according to claim 16 further comprising a tray and wherein the electrophoresis gel is located within the tray.

19. A package according to claim 18 wherein the tray has four side walls formed integral with a base, each side wall having a height less than the height of the electrophoresis gel when the electrophoresis gel is located within the tray.

20. A package according to claim 19 wherein the height of the side walls is between about 1% to about 5% shorter than the height of the electrophoresis gel when the electrophoresis gel is located within the tray.

21. A package according to claim 19 wherein the length and width of the tray are each between about 1% to about 2% larger than the length and width of the gel.

22. A package according to claim 18 wherein the tray has a thickness between about 0.010 inches and about 0.040 inches.

23. A package according to claim 18 wherein a plurality of electrophoresis gels are disposed within the tray.

24. A package according to claim 18 wherein a plurality of electrophoresis gels and trays disposed between the first and second sheets, each gel being located in an associated tray.

25. A package according to claim 16 wherein the at least one electrophoresis gel is an agarose gel.

26. A package according to claim 16 further comprising a support sheet disposed between at least one electrophoresis gel and the first sheet.

27. A package according to claim 16 wherein a plurality of electrophoresis gels are disposed within the cavity.

28. A package according to claim 27 wherein a spacer is located between adjacent electrophoresis gels.

29. A package according to claim 16 wherein the first sheet includes an outer layer of metallized polyester adhered to an inner layer of polyethylene.

30. An electrophoresis gel package comprising:
a pouch formed from first and second sheets that are sealed to one another along their edges to form an enclosed cavity, the cavity being at least partially evacuated of air;
at least one electrophoresis gel disposed within the cavity; and
a tray;
wherein the electrophoresis gel is located within the tray; and
wherein the tray has at least two opposed side walls, the side walls having a height no larger than the height of the electrophoresis gel when the gel is located within the tray.

31. A method of forming an evacuated package for an electrophoresis gel comprising the steps of:
providing a first sheet of packaging material;
placing an electrophoresis gel on the first sheet;
placing a second sheet of packaging material over the first sheet, the overlying edges of the first and second sheets defining the edges of the package and defining a cavity for the gel;
evacuating the air from between the first and second sheets without damaging the electrophoresis gel; and
sealing the edges of the package so as to enclose the gel therein;
wherein the air between the first and second sheets is evacuated so as to form a package upon sealing containing air at a pressure between about 11% and about 99% of atmospheric pressure.

32. A method of forming an evacuated package according to claim 31 wherein the electrophoresis gel is located within a tray, the tray being positioned between the first and second sheets.

33. A method of forming an evacuated package according to claim 31 wherein the air between the first and second sheets is evacuated so as to form a package upon sealing containing air at a pressure between about 60% and about 75% of atmospheric pressure.

* * * * *